United States Patent
Wiedemann et al.

(10) Patent No.: US 8,513,180 B2
(45) Date of Patent: Aug. 20, 2013

(54) ETHANOL-FREE PERFUME OIL MICROEMULSION

(75) Inventors: Joern Wiedemann, Holzminden (DE); Astrid Kaufhold, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/280,910

(22) Filed: Oct. 25, 2011

(65) Prior Publication Data

US 2012/0101020 A1  Apr. 26, 2012

Related U.S. Application Data

(60) Provisional application No. 61/406,285, filed on Oct. 25, 2010.

(51) Int. Cl.
*A61Q 13/00* (2006.01)
(52) U.S. Cl.
USPC .................................................. 512/1
(58) Field of Classification Search
USPC .................................................. 512/1
See application file for complete search history.

(56) References Cited

U.S. PATENT DOCUMENTS 5,468,725 A * 11/1995 Guenin et al. ............... 512/2
2003/0186836 A1  10/2003 Dumanois et al.

FOREIGN PATENT DOCUMENTS

| EP | 0334777 A1 * | 9/1989 |
| WO | WO 9521606 A1 * | 8/1995 |
| WO | WO-2005/123028 A1 | 12/2005 |
| WO | WO 2005123028 A1 * | 12/2005 |

* cited by examiner

*Primary Examiner* — Ling Choi
*Assistant Examiner* — Lanee Reuther
(74) *Attorney, Agent, or Firm* — Novak Druce Connolly Bove + Quigg LLP

(57) ABSTRACT

An ethanol-free perfume oil microemulsion is described, comprising or consisting of (a) water, (b) one or a plurality of vicinal diol(s), (c) one, two or three solvent(s) for reducing stickiness, selected from the group consisting of glycerol, isobutyric acid-1-hydroxy-2,2,4-trimethyl-3-pentyl ester and isobutyric acid-3-hydroxy-2,2,4-trimethyl-1-pentyl ester, and (d) one or a plurality of odor essence(s) and (e) optionally one or a plurality of further substances. Furthermore, uses and methods for reducing the stickiness of ethanol-free perfume oil microemulsions and articles comprising perfume oil microemulsions according to the invention are described.

18 Claims, No Drawings

ETHANOL-FREE PERFUME OIL MICROEMULSION

CROSS-REFERENCE TO RELATED APPLICATIONS

This application claims priority under 35 U.S.C. §119(e) to U.S. provisional application No. 61/406,285, filed Oct. 25, 2010, the entire contents of which is hereby incorporated by reference.

The present invention relates to ethanol-free perfume oil microemulsions, comprising or consisting of (a) water, (b) one or a plurality of vicinal diol(s), (c) one, two or three solvents for reducing stickiness, selected from the group consisting of glycerol, isobutyric acid-1-hydroxy-2,2,4-trimethyl-3-pentyl ester (compound of formula (1)) and isobutyric acid-3-hydroxy-2,2,4-trimethyl-1-pentyl ester (compound of formula (2)), and (d) one or a plurality of odor essence(s) and (e) one or a plurality of further substances.

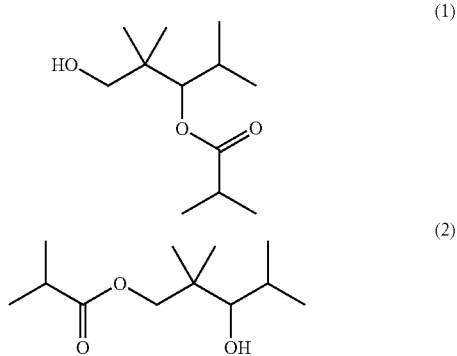

Moreover, the present invention relates to the use of glycerol, the compound of formula (1), the compound of formula (2) or a mixture comprising or consisting of glycerol, a compound of formula (1) and/or a compound of formula (2) for reducing the stickiness of an ethanol-free perfume oil microemulsion and a method of reducing the stickiness of an ethanol-free perfume oil microemulsion.

Moreover, the present invention relates to articles that comprise an ethanol-free perfume oil microemulsion according to the invention.

Further aspects of the present invention can be seen from the following description, the examples and the appended patent claims.

In the perfume industry there has long been a demand for aqueous, ethanol-free perfume oil compositions. Ethanol-containing solutions of perfume oils are certainly widely used, but such compositions have various drawbacks, which are sometimes unacceptable to the consumer. Objections to the use of ethanol in perfume oil compositions are based for example on a risk of skin irritations attributable to ethanol, religious reasons, or the carcinogenic potential of ethanol, as well as legal regulations on avoidance of volatile organic substances (VOCs). This contrasts with the acceptance of aqueous formulations, which are nonflammable and are generally regarded as harmless by consumers. Accordingly, in the past the perfume industry has already attempted to develop suitable, ethanol-free perfume oil compositions. However, so far it has not been possible to provide ethanol-free perfume oil compositions that have been accepted (without qualification) by the consumer.

Ethanol-free perfume oil compositions known in the prior art as a rule contain—along with perfume oil(s), water and optionally preservative(s)—one or a plurality of surfactants, which are used for solubilizing the perfume oil or oils. Surfactants can, however, cause skin irritations and as a rule result in the perfume composition feeling sticky, in the opinion of consumers.

US 2003/0186836 A1 describes alcohol-free, aqueous perfume oil compositions, which contain isoprene glycol (3-methyl-1,3-butanediol) as solvent (instead of ethanol). However, the perfume oil compositions described in US 2003/0186836 A1 contain, additionally, one or a plurality of surfactants, so that these are rejected by the consumer, because of the resultant stickiness.

WO 2005/123028 A1 describes an ethanol-free, perfumed, aqueous microemulsion, which comprises a vicinal diol as solvent. Admittedly, according to WO 2005/123028 A1, surfactants are only contained optionally in the microemulsion. However, it turns out that the microemulsions described in WO 2005/123028 A1 nevertheless feel sticky, in the view of consumers, on account of the diols they contain.

Thus, there is still interest in providing ethanol-free perfume oil compositions with reduced stickiness. Moreover, substances that have marketing authorization for the corresponding use should preferably be used exclusively. Furthermore, it is desirable for said perfume oil compositions to be transparent, to ensure varied possible applications in the perfume industry.

The main object to be achieved by the present invention was therefore to provide an ethanol-free perfume oil composition that has stickiness that is reduced or is not perceived by consumers as disturbing and preferably satisfies the requirements mentioned above.

Another object to be achieved by the present invention was to provide uses and methods by which the stickiness of ethanol-free perfume oil compositions can be reduced.

Moreover, an object to be achieved by the present invention was to provide articles that contain an ethanol-free perfume oil composition with reduced stickiness as described above.

Further objects forming the basis of the present invention can be seen from the present description, the examples and in particular the appended patent claims.

The main object to be achieved by the present invention is achieved with an ethanol-free perfume oil microemulsion, comprising or consisting of:
(a) water,
(b) one or a plurality of vicinal diol(s),
(c) one, two or three solvent(s) for reducing stickiness, selected from the group consisting of glycerol, isobutyric acid-1-hydroxy-2,2,4-trimethyl-3-pentyl ester (compound of formula (1)) and isobutyric acid-3-hydroxy-2,2,4-trimethyl-1-pentyl ester (compound of formula (2)),
(d) one or a plurality of odor essence(s), and
(e) optionally one or a plurality of further substances.

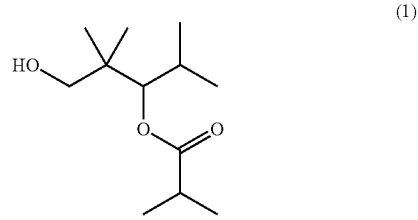

-continued

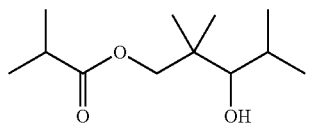
(2)

For the purposes of the present invention the constituent or constituents (d) is/are not selected from the group consisting of glycerol, isobutyric acid-1-hydroxy-2,2,4-trimethyl-3-pentyl ester (compound of formula (1)) and isobutyric acid-3-hydroxy-2,2,4-trimethyl-1-pentyl ester (compound of formula (2)).

As mentioned above, the present invention relates to ethanol-free perfume oil microemulsions. An "ethanol-free" perfume oil microemulsion means, in the context of the present invention, a completely or at least substantially ethanol-free perfume oil microemulsion. Accordingly, a perfume oil microemulsion according to the invention preferably comprises no ethanol or less than 0.01 wt. % ethanol, preferably less than 0.001 wt. % ethanol, relative to the total weight of the perfume oil microemulsion.

The term "microemulsion" denotes, in the context of the present invention, a macroscopically homogeneous, optically transparent and thermodynamically stable mixture, comprising
at least one hydrophilic,
at least one lipophilic and
at least one amphiphilic substance.

A microemulsion comprises a hydrophilic phase, a lipophilic phase and an amphiphilic phase. In a perfume oil microemulsion according to the invention, the hydrophilic phase preferably contains constituent (a), i.e. water, and optionally glycerol (constituent (c)) and optionally one or a plurality of further substances according to constituent (e), e.g. preservatives, colorants and/or hydrophobic light-stability agents. The lipophilic phase preferably comprises constituent (d), e.g. in the form of a perfume oil, or one or a plurality of the odor essences according to constituent (d) and optionally isobutyric acid-1-hydroxy-2,2,4-trimethyl-3-pentyl ester (compound of formula (1)) and/or isobutyric acid-3-hydroxy-2,2,4-trimethyl-1-pentyl ester (compound of formula (2)) (constituent (c)), and optionally one or a plurality of substances according to constituent (e), e.g. preservatives, lipophilic light-stability agents, colorants and/or stabilizers, in particular radical absorbers. The amphiphilic phase preferably comprises one or a plurality of vicinal diols according to constituent (b) and optionally one or a plurality of constituents of a perfume oil that is present. Depending on the substances or constituents contained in a perfume oil microemulsion according to the invention the aforementioned substances can optionally also be arranged or located in another phase than that mentioned above, e.g. it is possible for one or a plurality of the vicinal diols according to constituent (b) to be located in the hydrophilic or lipophilic phase.

A "perfume oil" (alone) comprises for the purposes of the present invention preferably less than 10 wt. % of carrier substances, preferably no carrier substances, in particular no dipropylene glycol, diethyl phthalate, triethyl citrate or isopropyl myristate, but consists substantially of odor essences. Accordingly a perfume oil microemulsion according to the invention is preferably (essentially) free from (such) carrier substances.

Perfume oils are used in particular for making perfumes, by putting them in solutions, which on evaporation "entrain" the odor essences and thus impart to the olfactory organ of the user, i.e. of the person, the sensory impression of a particular odor. Besides being used in perfumes, eau de parfum, or eau de toilette, perfume oils are often also used for producing a certain fragrance in residential rooms, for example use in fragrance lamps, atomizers or diffusers. Furthermore, perfume oils can also be used in countless other articles or preparations, for example from shoe creams to hair shampoos, in lavatory cleaners, washing powders or cat litter.

It was particularly surprising that the constituents (c) of a perfume oil microemulsion according to the invention advantageously allow the stickiness of ethanol-free perfume oil microemulsions to be reduced particularly well (see below, test example).

Another advantage of perfume oil microemulsions according to the invention is that, relative to ethanol-containing and partly also ethanol-free perfume oil compositions known in the prior art, for the consumer they cause less sensation of drying of the skin (see below, test example).

Advantageously, a perfume oil microemulsion according to the invention is also thermodynamically stable and does not separate at temperatures that usually prevail in households, preferably at temperatures in the range from 0 to 40° C.

Moreover, constituents (b) and (c), in particular the solvents (c), advantageously do not lead to clouding of the perfume oil microemulsion. Furthermore, the solvents (c) are advantageously authorized for use in cosmetic agents or preparations.

As already mentioned, the solvents (c) are advantageously suitable for reducing the stickiness of ethanol-free perfume oil microemulsions. Apart from the solvents (c), a perfume oil microemulsion according to the invention can also contain—as constituent(s) (e)—further substances for reducing stickiness. However, an ethanol-free perfume oil microemulsion according to the invention as described above, wherein the perfume oil microemulsion comprises a total amount of solvents (c) that is sufficient to reduce the stickiness of the perfume oil microemulsion (significantly) in comparison with an identical perfume oil microemulsion without solvents (c), is particularly preferred.

In the context of the present invention, preferably linear vicinal diols, in particular vicinal diols with five to eight carbon atoms, are used as vicinal diols (b). One or a plurality of or all of the vicinal diols (b) selected from the group consisting of 2-pentanediol, 1,2-hexanediol, 1,2-heptanediol and 1,2-octanediol is/are particularly preferred. The vicinal diols (b) can be used either alone or in any combination with one another.

An ethanol-free perfume oil microemulsion as described above, wherein the or one of the vicinal diols (b) is 1,2-hexanediol, is particularly preferred. Particularly for the case when a perfume oil microemulsion according to the invention contains exactly one vicinal diol, this is preferably 1,2-hexanediol.

If a perfume oil microemulsion according to the invention comprises two or a plurality of vicinal diols (b), preferably 1,2-pentanediol and 1,2-octanediol are used. Perfume oil microemulsions according to the invention comprising 1,2-pentanediol and 1,2-octanediol and optionally one or a plurality of further diols, wherein the ratio of the total amount of 1,2-pentanediol to 1,2-octanediol in the perfume oil microemulsion, based on weight, is preferably in the range from 6 to 1 to 2 to 1, preferably in the range from 5 to 1 to 3 to 1, and particularly preferably is about 4 to 1, are particularly preferred.

As was found in our own research, the compounds of formulae (1) and (2), as described above, are particularly preferred for the purposes of the present invention. By using these compounds, the stickiness of ethanol-free perfume oil microemulsions, in particular in combination with diols (b) described above, to be used according to the invention, can be reduced particularly well (see below, test example). Moreover, the compounds of formulae (1) and (2) advantageously have no or only a very faint intrinsic odor, so that they are particularly suitable for the purposes of the present invention.

Accordingly, an ethanol-free perfume oil microemulsion according to the invention is particularly preferred wherein the or two of the solvents (c) are isobutyric acid-1-hydroxy-2,2,4-trimethyl-3-pentyl ester (compound of formula (1)) and isobutyric acid-3-hydroxy-2,2,4-trimethyl-1-pentyl ester (compound of formula (2)). More preferably, in said perfume oil microemulsion the ratio of the total amount of isobutyric acid-1-hydroxy-2,2,4-trimethyl-3-pentyl ester (compound of formula (1)) to isobutyric acid-3-hydroxy-2,2,4-trimethyl-1-pentyl ester (compound of formula (2)) in the perfume oil microemulsion, based on weight, is 99:1 to 1:99, preferably 70:30 to 30:70, preferably in the range from 60:40 to 40:60, particularly preferably about 44:56.

The or one, a plurality of or all odor essences (b) of an ethanol-free perfume oil microemulsion according to the invention is or are preferably selected from the group consisting of: 1-phenyl-2-methyl-2-propyl acetate, 2-methyl butylbutyrate, aldron (4-[(3,3-dimethylbicyclo[2.2.1]hept-2-yl) methyl]-2-methylcyclohexanone), allyl-2-cyclohexyloxyglycolate, allyl-2-pentyloxyglycolate, allyl-3-cyclohexylpropionate, allylcapronate, Amarocit (1,1-dimethoxy-2,2,5-trimethyl-4-hexene), Ambral (dodecahydro-3,8,8,11a-tetramethyl-5H-3,5a-epoxynaphth [2.1-c]oxepine), ambrettolide (9-hexadecen-16-olide), Ambrinol S (1,2,3,4,4a,5,6,7-octahydro-2,6,6-trimethyl-2-napthalinol), Ambrinol epoxide, Ambrocenide (4aR,5R,7aS, 9R)-octahydro-2,2,5,8,8,9a-hexamethyl-4H-4a,9-methanoazuleno(5,6-d)-1,3-dioxol), Ambroxide (3a,6,6,9a-tetramethyldodecahydronaphtho[2,1-b]-furan), amyl formate, aurelione (7-cyclohexadecen-1-one and 8-cyclohexadecen-1-one), Boronal [2-methyl-4-(2,6,6-trimethyl-1-cyclohexen-1-yl)-butenal], Brahmanol [2-methyl-4-(2,2,3-trimethyl-3-cyclopentenyl)-butanol], buccoximes (1,5-dimethylbicyclo[3,2,1]octane-8-one oxime), butyl acetate, cantryl (2,2,3-trimethyl-3-cyclopentenyl-1-acetonitrile), Cassix 150 (4-methoxy-2-methyl-2-butanethiol), chrysanthemum [1-(2,4-dimethyl-3-cyclohexen-1-yl)-2,2-dimethyl-1-propanone], cis-3-hexenyl acetate, citronellyl butyrate, citronellyl tiglinate (3,7-dimethyl-6-octenyl-2-methylcrotonate), citronitrile (3-methyl-5-phenyl-2-pentenenitrile), Citrowanil B (alpha-ethenyl-alpha-methylbenzene propanenitrile), Claritone (2,4,7-tetramethyl-6-octen-3-one), Corps Racine VS [2-(3-phenylpropyl) pyridine], coumarone (1-(2-benzofuranyl)-ethanone), cyclogalbanate (allylcyclohexyloxyacetate), cyclohexylmagnol (alpha-methyl-cyclohexanepropanol), Datilat (1-cyclohexylethylcrotonate), ethyl-2-methyl butyrate, ethylisobutyrate, ethylisovalerate, ethyltricyclo[5,2,1,0$^{2,6}$]decan-2-ylcarboxylate, Farenal (2,6,10-trimethyl-9-undecenal), Filbertone (5-methyl-2-hepten-4-one), Fleursandol (4-(3a,4, 5,6,7,7a-hexahydro-4,7-methano-1H-inden-6-yl)-3-methyl-3-buten-2-ol), Florazon (4-ethyl-alpha,alpha-dimethylbenzene propanal), Floropal (2,4,6-trimethyl-4-phenyl-1,3-dioxane), Fragolane [(2,4-dimethyl-[1,3]dioxolan-2-yl)ethyl acetates)], Frutinate (but-2-enoic acid-1,3-dimethyl butyl ester), gamma-decalactones, geranyl acetate, geranyl butyrate, geranyl tiglinate (trans-3,7-dimethyl-2,6-octadienyl-2-methylcrotonate), Globalide [(11/12)-pentadecen-15-olide], globanone (8-cyclohexadecen-1-one), hexyl butyrate, hydrocitronitrile (beta-methyl-benzene pentane nitrile), Indianol (4-[3a,4,5,6,7,7a-hexahydro-4,7-methano-1H-inden-5 (6)-yl]-3-methyl-3-buten-2-ol), Indoflor (4,4a,5,9b-tetrahydoindeno[1,2-d]-m-dioxin), irisnitrile (2-nonenylnitrile), isoamyl acetate, isoamylisovalerate, isodamascone [1-(2,4,4-trimethyl-2-cyclohexen-1-yl)-2-buten-1-one], isomuscone (cyclohexadecanone), Jacinthaflor (2-methyl-4-phenyl-1,3-dioxolane), ketamber (dodecahydro-3,8,8,11a-tetramethyl-5H-3,5a-epoxynaphth[2,1-c]oxepine), lactojasmone (4-hexyl-4-methyl-butyrolactone), Leguminal (propanal-methyl-cis-3-hexenyl-acetal), macrolides (oxacyclohexadecan-2-one), madranol (mixture of various hexahydromethylionones), magnolane (2,4-dimethyl-5,6-indeno-1,3-dioxane), majantol [2,2-dimethyl-3-(3-methylphenyl)-propanol], mandaril (3,12-tridecadiene nitrile), menthyl acetate, methyl butyrate, methyl dihydrojasmonate, methylisobutyrate, mintonate (3,3,5-trimethylcyclohexyl acetate), mugetanol [1-(4-isopropylcyclohexyl)-ethanol], nerolione [1-(3-methyl-2-benzofuranyl)-ethanone], octyl acetate, ozonil (2-tridecene nitrile), palisandal (1,1-dimethoxycyclododecane), palisandin (cyclododecylmethyl ether), parmanyl [3-(cis-3-hexenyloxy)-propanenitrile], passifloran (3-acetylthiohexyl acetate), peacholide (cis- and trans-3-methyl-gamma-decalactone), prenylsalicylate, profarnesal (2,6,10-trimethyl-5,9-undecadienal), Projasmon P (2-heptylcyclopentanone), pyroprunate (but-2-enoic acid bicyclopenten-2-yl ester), rholiate (carbonic acid-ethyl-2,3,6-trimethylcyclohexyl ester), rosaphen (2-methyl-5-phenylpentan-1-ol), rose oxide, Sandel 80 (trans-3-isocamphylcyclohexanol), sandranol (2-ethyl-4-(2,2,3-trimethyl-3-cyclopenten-1-yl)-2-buten-1-ol), symrose (4-isoamylcyclohexanol), symroxane (4-(3-methylbutyl)-cyclohexanol (Z)), tabanone [4-(2-butenylidene)-3,4,5-trimethyl-2-cyclohexen-1-one], terpineol-4, timberol (2,2,6-trimethyl-alpha-propyl-cyclohexanpropanol), tolyl acetate aldehyde D para (4-methyl-benzene acetaldehyde), tricyclodecenylpropionate, tropicol (2-mercapto-2-methyl-pentan-1-ol), vertosine [2-(2,4-(or 3,5)-dimethyl-3-cyclohexen-1-yl)-methylene-aminobenzoic acid methyl ester], vertral (octahydro-4,7-methano-1H-indene-carbaldehyde), vetikolacetate (1,3-dimethyl-3-phenylbutyl acetate), vetival (4-cyclohexyl-4-methylpentan-2-one), Ysamber K (spiro hexahydro-1',1',5',5'-tetramethyl-[1,3-dioxolane-2,8'-(5'H)-[2H-2,4a]-methanonaphthalene], individual odor essences from the hydrocarbons group, e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane; the aliphatic alcohols e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5, 6,6-pentamethyl-3/4-hepten-2-ol and 3,5,6,6-tetramethyl-4-methylene-heptan-2-ol; (E,Z)-2,6-nonadienol; 3,7-dimethyl-7-methoxyoctan-2-ol; 9-decenol; 10-undecenol; 4-methyl-3-decen-5-ol; the aliphatic aldehydes and acetals thereof e.g. hexanal; heptanal; octanal; nonanal; decanal; undecanal; dodecanal; tridecanal; 2-methyloctanal; 2-methylnonanal; (E)-2-hexenal; (Z)-4-heptenal; 2; 6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxy-propoxy)-(E/Z)-3-hexene; the aliphatic ketones and oximes thereof e.g. 2-heptanone; 2-octanone; 3-octanone; 2-nonanone; 5-methyl-3-heptanone; 5-methyl-3-heptanone-oxime; 2,4,4,7-tetramethyl-6-octen-3-one; 6-methyl-5-hepten-2-one; the aliphatic sulfur-containing compounds e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; the aliphatic nitriles e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile; the esters of aliphatic carboxylic acids e.g. (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexylcrotonate; ethylisovalerate; ethyl-2-methylpentanoate; ethylhexanoate; allylhexanoate; ethylheptanoate; allylheptanoate; ethyloctanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentylcrotonate; the acyclic terpene alcohols e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof; the acyclic terpene aldehydes and ketones e.g. geranial; neral; citronellal; 7-hydroxy-3,7-dimethyloctanal; 7-methoxy-3,7-dimethyloctanal; 2,6,10-trimethyl-9-undecenal; geranyl-acetone; and the dimethyl and diethyl acetals of geranial, neral, 7-hydroxy-3,7-dimethyloctanal; the cyclic terpene alcohols e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof; the cyclic terpene aldehydes and ketones e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damasceone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methylcedryl ketone); the cyclic alcohols e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol; the cycloaliphatic alcohols e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol; the cyclic and cycloaliphatic ethers e.g. cineol; cedrylmethyl ether; cyclododecylmethyl ether; 1,1-dimethoxycyclododecane; (ethoxymethoxy)cyclododecane; alpha-cedrene-epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane; the cyclic and macrocyclic ketones e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4 (5H)-indanone; 8-cyclohexadecen-1-one; 9-cycloheptadecen-1-one; cyclopentadecanone; cyclohexadecanone; the cycloaliphatic aldehydes e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde; the cycloaliphatic ketones e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenylmethyl ketone; methyl-2,6,10-trimethyl-2,5,9-cyclododecatrienyl ketone; tert.-butyl-(2,4-dimethyl-3-cyclohexen-1-yl) ketone; the esters of cyclic alcohols e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenylpropionate; 4,7-methano-3a,4,5,6,7,7a-hexahydro-5, or 6-indenylisobutyrate; 4,7-methanooctahydro-5, or 6-indenyl acetate; the esters of cycloaliphatic alcohols e.g. 1-cyclohexylethylcrotonate; the esters of cycloaliphatic carboxylic acids e.g. allyl-3-cyclohexylpropionate; allylcyclohexyloxyacetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexenecarboxylate; ethyl-2,3,6,6-tetramethyl-2-cyclohexenecarboxylate; ethyl-2-methyl-1,3-dioxolane-2-acetate; the araliphatic alcohols e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol; the esters of araliphatic alcohols and aliphatic carboxylic acids e.g. benzyl acetate; benzyl propionate; benzyl isobutyrate; benzyl isovalerate; 2-phenylethyl acetate; 2-phenylethylpropionate; 2-phenylethylisobutyrate; 2-phenylethylisovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethylisobutyrate; 4-methoxybenzyl acetate; the araliphatic ethers e.g. 2-phenylethylmethyl ether; 2-phenylethylisoamyl ether; 2-phenylethyl-1-ethoxyethyl ether; phenylacetaldehyde-dimethylacetal; phenylacetaldehyde-diethylacetal; hydratropa-aldehyde dimethylacetal; phenylacetaldehyde-glycerinacetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin; the aromatic and araliphatic aldehydes e.g. benzaldehyde; phenylacetaldehyde; 3-phenylpropanal; hydratropa-aldehyde; 4-methylbenzaldehyde; 4-methylphenylacetaldehyde; 3-(4-ethylphenyl)-2,2-dimethylpropanal; 2-methyl-3-(4-isopropylphenyl) propanal; 2-methyl-3-(4-tert.-butylphenyl)propanal; 2-methyl-3-(4-isobutylphenyl)propanal; 3-(4-tert.-butylphenyl)propanal; cinnamaldehyde; alpha-butyl cinnamaldehyde; alpha-amyl cinnamaldehyde; alpha-hexyl cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene dioxybenzaldehyde; 3,4-dimethoxybenzaldehyde; 2-methyl-3-(4-methoxyphenyl) propanal; 2-methyl-3-(4-methylene dioxyphenyl)propanal; the aromatic and araliphatic ketones e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethyl ketone; 6-tert.-butyl-1,1-dimethyl-4-indanylmethyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone; the aromatic and araliphatic carboxylic acids and esters thereof e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allylphenoxyacetate; methylsalicylate; isoamylsalicylate; hexylsalicylate; cyclohexylsalicylate; cis-3-hexenylsalicylate; benzyl salicylate; phenylethylsalicylate; methyl-2,4-dihydroxy-3,6-dimethyl benzoate; ethyl-3-phenylglycidate; ethyl-3-methyl-3-phenylglycidate; the nitrogen-containing aromatic compounds e.g. 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methy-N-methylanthranilate; Schiff's bases of methylanthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; 2-(3-phenylpropyl)pyridine; indole; skatole; 2-methoxy-3-isopropylpyraxine; 2-isobutyl-3-methoxypyrazine; the phenols, phenyl ethers and phenyl esters e.g. estragole; anethole; eugenol; eugenylmethyl ether; isoeugenol; isoeugenylmethyl ether; thymol; carvacrol; diphenyl ether; beta-naphthylmethyl ether; beta-naphthylethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate; the heterocyclic compounds e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; the lactones e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

The or one, a plurality of or all odor essences contained in an ethanol-free perfume oil microemulsion according to the invention can also be contained in a perfume oil microemulsion according to the invention in the form of extracts from natural raw materials, for example in the form of essential oils, concretes, absolutes, resins, resinoids, balsams or tinctures, preferably those from the group consisting of: ambergris tincture; amyris oil; angelica seed oil; angelica root oil; anise oil; valerian oil; basil oil; tree moss absolute; bay oil; mugwort oil; benzoic resin; bergamot oil; beeswax absolute; birch tar oil; bitter almond oil; savory oil; bucho leaf oil; cabreuva oil; cade oil; calamus oil; camphor oil; cananga oil; cardamom oil; cascarilla oil; cassia oil; cassia absolute; castoreum absolute; cedar leaf oil; cedar wood oil; cistus oil; citronellol; lemon oil; copaiba balsam; copaiba balsam oil; coriander oil; costus root oil; cumin oil; cypress oil; davana oil; dill oil; dill seed oil; eau de brouts absolute; oak moss absolute; elemi oil; tarragon oil; eucalyptus-citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea-cubeba oil; bay leaf oil; mace oil; marjoram oil; mandarin oil; massoy bark oil; mimosa absolute; musk seed oil; musk tincture; muscatel-sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir-needle oil; tea tree oil; turpentine oil; thyme oil; tolu balsam; tonka absolute; tuberose absolute; vanilla extract; violet leaf absolute; verbena oil; vetiver oil; Juniper berry oil; wine lees oil; wormwood oil; wintergreen oil; ylang-ylang oil; hyssop oil; civet absolute; cinnamon leaf oil; cinnamon bark oil and fractions thereof, or ingredients isolated therefrom.

The proportion of water in an ethanol-free perfume oil microemulsion according to the invention is advantageously in the range 30-90 wt. %, preferably in the range 40-70 wt. %, particularly preferably in the range 45-55 wt. %, relative to the total weight of the perfume oil microemulsion.

An ethanol-free perfume oil microemulsion according to the invention preferably comprises one or a plurality of vicinal diols (b) in a total amount of 5-50 wt. %, preferably 10-40 wt. %, particularly preferably 25-35 wt. %, relative to the total weight of the perfume oil microemulsion.

The total amount of solvents (c), in particular the total amount of compounds of formulae (1) and (2), in a perfume oil microemulsion according to the invention is preferably 1-20 wt. %, preferably 2-10 wt. %, particularly preferably 3-5 wt. %, relative to the total weight of the perfume oil microemulsion.

The amount of odor essences (d) contained in a perfume oil microemulsion according to the invention will be selected by a person skilled in the art according to the desired fragrance intensity. Preferably a perfume oil microemulsion according to the invention comprises a total amount of odor essences (d)

in the range 1-50 wt. %, preferably in the range 2-30 wt. %, more preferably in the range 4-10 wt. %, particularly preferably in the range 5-7 wt. %, relative to the total weight of the perfume oil microemulsion.

To summarize, a perfume oil microemulsion according to the invention is particularly preferred wherein, in each case relative to the total weight of the perfume oil microemulsion, the total amount of water (a) in the perfume oil microemulsion is 30-90 wt. %, preferably 40-70 wt. %, particularly preferably 45-55 wt. %, and/or the total amount of vicinal diols (b) in the perfume oil microemulsion is 5-50 wt. %, preferably 10-40 wt. %, particularly preferably 25-35 wt. %, and/or the total amount of solvents (c) in the perfume oil microemulsion is 1-20 wt. %, preferably 2-10 wt. %, particularly preferably 3-5 wt. %, and/or the total amount of odor essences (d) in the perfume oil microemulsion is 1-50 wt. %, preferably 2-30 wt. %, more preferably 4-10 wt. %, particularly preferably 5-7 wt. %.

As already mentioned, the solvents (c), in particular the compounds of formulae (1) and (2), advantageously do not lead to clouding of a perfume oil microemulsion according to the invention. A perfume oil microemulsion according to the invention preferably has a nephelometric turbidity unit (NTU) value of less than 6.

An ethanol-free perfume oil microemulsion according to the invention comprises, as described above, preferably one or a plurality of further substances (e). These are preferably selected from the group consisting of substances that alter the appearance and/or viscosity of the perfume oil microemulsion, for example antifoaming agents, thickeners or optionally colorants, substances that protect the perfume oil microemulsion, for example preservatives, complexing agents, stabilizers, antioxidants or light protection filters, and substances that have an additional benefit for the user, for example cosmetic active substances.

Another aspect of the present invention relates to the use of glycerol, isobutyric acid-1-hydroxy-2,2,4-trimethyl-3-pentyl ester (compound of formula (1)) or isobutyric acid-3-hydroxy-2,2,4-trimethyl-1-pentyl ester (compound of formula (2)) or a mixture comprising or consisting of glycerol, isobutyric acid-1-hydroxy-2,2,4-trimethyl-3-pentyl ester (compound of formula (1)) and/or isobutyric acid-3-hydroxy-2,2,4-trimethyl-1-pentyl ester (compound of formula (2)) for reducing the stickiness of an ethanol-free perfume oil microemulsion.

A use according to the invention as described above is particularly preferred, wherein the perfume oil microemulsion comprises one or a plurality of vicinal diol(s), wherein the or one, a plurality of or all the vicinal diols is or are preferably selected from the group consisting of vicinal diols with 5 to 8 carbon atoms, preferably from the group consisting of 1,2-pentanediol, 1,2-hexanediol, 1,2-heptanediol and 1,2-octanediol.

A use according to the invention as described above is further preferred, wherein the or one of the vicinal diols is 1,2-hexanediol. Particularly for the case when the perfume oil microemulsion contains exactly one vicinal diol, this is preferably 1,2-hexanediol. If the perfume oil microemulsion comprises two or a plurality of vicinal diols, they are then preferably 1,2-pentanediol and 1,2-octanediol. Particularly preferably the perfume oil microemulsion comprises 1,2-pentanediol and 1,2-octanediol and optionally one or a plurality of further diols, wherein the ratio of the total amount of 1,2-pentanediol to 1,2-octanediol in the perfume oil microemulsion, based on weight, is preferably in the range from 6 to 1 to 2 to 1, preferably in the range from 5 to 1 to 3 to 1, and particularly preferably is about 4 to 1.

A use according to the invention, preferably a use as already described as preferable, is particularly preferred, wherein a mixture comprising or consisting of a compound of formula (1) and a compound of formula (2) is used, wherein the ratio of the total amount of compound of formula (1) to the total amount of compound of formula (2) in the mixture, based on weight, is preferably in the range from 99:1 to 1:99, preferably in the range from 70:30 to 30:70, preferably in the range from 60:40 to 40:60, and particularly preferably is about 44:56.

Another aspect of the present invention relates to a method of reducing the stickiness of an ethanol-free perfume oil microemulsion, comprising the following steps:

providing an ethanol-free perfume oil microemulsion and adding glycerol, isobutyric acid-1-hydroxy-2,2,4-trimethyl-3-pentyl ester (compound of formula (1)) or isobutyric acid-3-hydroxy-2,2,4-trimethyl-1-pentyl ester (compound of formula (2)) or a mixture comprising or consisting of glycerol, isobutyric acid-1-hydroxy-2,2,4-trimethyl-3-pentyl ester (compound of formula (1)) and/or isobutyric acid-3-hydroxy-2,2,4-trimethyl-1-pentyl ester (compound of formula (2)) to the perfume oil microemulsion in an amount that is sufficient to reduce (significantly) the stickiness of the perfume oil microemulsion.

Following the addition of glycerol, of a compound of formula (1) and/or of a compound of formula (2) or of a corresponding mixture, as described above, preferably an ethanol-free perfume oil microemulsion according to the invention as described above is formed, particularly preferably an ethanol-free perfume oil microemulsion according to the invention previously designated as preferable. Accordingly, what has been said previously applies correspondingly to the constituents of said perfume oil microemulsion, in particular to the amounts or proportions of the respective constituents.

A method according to the invention wherein the perfume oil microemulsion provided comprises one or a plurality of vicinal diol(s) is also preferred.

A method according to the invention, as described above, is particularly preferred, wherein the or one, a plurality of or all the vicinal diols is or are selected from the group consisting of vicinal diols with 5 to 8 carbon atoms, preferably from the group consisting of 1,2-pentanediol, 1,2-hexanediol, 1,2-heptanediol and 1,2-octanediol. Incidentally, what was said previously regarding the vicinal diols (b) applies correspondingly to selection of the vicinal diols.

A method according to the invention as described above is particularly preferred, wherein a mixture comprising or consisting of isobutyric acid-1-hydroxy-2,2,4-trimethyl-3-pentyl ester (compound of formula (1)) and isobutyric acid-3-hydroxy-2,2,4-trimethyl-1-pentyl ester (compound of formula (2)) is added to the perfume oil microemulsion. Preferably the ratio of the total amount of isobutyric acid-1-hydroxy-2,2,4-trimethyl-3-pentyl ester to isobutyric acid-3-hydroxy-2,2,4-trimethyl-1-pentyl ester in the mixture, based on weight, is then 99:1 to 1:99, more preferably 70:30 to 30:70, preferably 60:40 to 40:60. Particularly preferably the ratio of the total amount of isobutyric acid-1-hydroxy-2,2,4-trimethyl-3-pentyl ester to isobutyric acid-3-hydroxy-2,2,4-trimethyl-1-pentyl ester in the mixture, based on weight, is about 44:56.

Another aspect of the present invention relates to an article comprising or consisting of an ethanol-free perfume oil microemulsion according to the invention as described above, preferably a perfume oil microemulsion according to the invention designated above as preferable.

Preferably an article according to the invention is selected from the group consisting of eau de toilette, deodorants, air fresheners, room and laundry sprays, preferably from the group consisting of eau de toilette, room and laundry sprays. Preferably an article according to the invention is not in the form of cream, deodorant stick or wax crayon.

A perfume oil microemulsion according to the invention can advantageously be produced by mixing together the constituents of the microemulsion, in particular the constituents (a) to (e), as described above in each case, in any order (or simultaneously). However, depending on the constituent to be used, certain usual measures known by a person skilled in the art may be necessary. For example, 1,2-octanediol (as vicinal diol (b)) should preferably be warmed before being added to the other constituents of the microemulsion, to improve dissolution.

EXAMPLES

Test Example 15 testers participated in a panel test, to assess various perfume oil compositions. The following criteria were to be assessed:
stickiness on the skin from 0 (not sticky) to 3 (very sticky) and
drying of the skin from 0 (not drying) to 3 (very drying).
The following four perfume oil compositions were assessed by each tester:
A) eau de toilette (EdT): 5 wt. % perfume oil "Bioman" (cf. examples of application 1 to 3), 95 wt. % of 80% ethanol
B) EdT: 5 wt. % perfume oil "Bioman" (cf. examples of application 1 to 3), 28 wt. % 1,2-pentanediol, 7 wt. % 1,2-octylene glycol, 60 wt. % water
C) EdT: composition according to example of application 1 (see below)
D) EdT: composition according to example of application 2 (see below)

Result:

| Composition | Stickiness (0-3) | Drying (0-3) |
| --- | --- | --- |
| A) | 0.26 | 1.74 |
| B) | 0.84 | 0.45 |
| C) | 0.67 | 0.40 |
| D) | 0.47 | 0.25 |

As can be seen from the results, addition of the vicinal diols (see ethanol-free composition B)) relative to the ethanol-containing composition A) results in increased stickiness (0.84) but reduced drying properties (0.45).

With solvents (c) contained in a perfume oil microemulsion according to the invention (see ethanol-free compositions C) and D)), with further reduced drying properties (0.40 or 0.25), advantageously reduced stickiness (0.67 or 0.47) can be achieved relative to composition B).

Examples of Application

Example of application 1 (ethanol-free perfume oil microemulsion):

| Ingredient | Designation | wt. % |
| --- | --- | --- |
| Bioman | Perfume oil* (Symrise) | 5.0 |
| Hydrolite-5 | 1,2-Pentanediol | 28.0 |
| Hydrolite-8 | 1,2-Octanediol | 7.0 |
| Water | Water | 50.0 |
| Glycerol | Glycerol | 10.0 |
| Total | | 100.0 |

*containing at least 92 wt. % odor essence(s)

Example of application 2 (ethanol-free perfume oil microemulsion):

| Ingredient | Designation | wt. % |
| --- | --- | --- |
| Bioman | Perfume oil (Symrise) | 5.0 |
| Hydrolite-5 | 1,2-Pentanediol | 28.0 |
| Hydrolite-8 | 1,2-Octanediol | 7.0 |
| Water | Water | 50.0 |
| Symfresh NX | 1) | 10.0 |
| Total | | 100.0 |

1) consisting of the compound of formula (1) and the compound of formula (2), as described above in each case, wherein the ratio of the total amount of compound of formula (1) to the total amount of compound of formula (2), based on weight, is about 44:56.

Example of application 3 (ethanol-free perfume oil microemulsion):

| Ingredient | Designation | wt. % |
| --- | --- | --- |
| Bioman | Perfume oil (Symrise) | 5.0 |
| Hydrolite-5 | 1,2-Pentanediol | 29.0 |
| Hydrolite-8 | 1,2-Octanediol | 6.0 |
| Water | Water | 55.0 |
| Symfresh NX | (see example of application 2) | 5.0 |
| Total | | 100.0 |

Example of application 4 (ethanol-free perfume oil microemulsion):

| Ingredient | Designation | wt. % |
| --- | --- | --- |
| Open Seas | Perfume oil* (Symrise) | 7.0 |
| Hydrolite-5 | 1,2-Pentanediol | 22.0 |
| Hydrolite-8 | 1,2-Octanediol | 5.5 |
| Water | Water | 58.0 |
| Glycerol | Glycerol | 7.5 |
| Total | | 100.0 |

*containing at least 96 wt. % odor essence(s)

The invention claimed is:
1. An ethanol-free perfume oil microemulsion, comprising:
(a) water;
(b) at least one vicinal diol;
(c) one or two solvent(s) for reducing stickiness, wherein one or two solvent(s) is/are selected from the group consisting of isobutyric acid-1-hydroxy-2,2,4-trimethyl-3-pentyl ester and isobutyric acid-3-hydroxy-2,2,4-trimethyl-1-pentyl ester; and
(d) at least one odor essence.

2. The ethanol-free perfume oil microemulsion as claimed in claim 1, wherein the amount of solvents (c) is sufficient to reduce the stickiness of the perfume oil microemulsion in comparison with an identical perfume oil microemulsion without solvent (c).

3. The ethanol-free perfume oil microemulsion as claimed in claim 1, wherein the at least one vicinal diol (b) is selected from the group consisting of vicinal diols with 5 to 8 carbon atoms.

4. The ethanol-free perfume oil microemulsion as claimed in claim 3, wherein the at least one vicinal diol (b) is selected from the group consisting of 1,2-pentanediol, 1,2-hexanediol, 1,2-heptanediol and 1,2-octanediol.

5. The ethanol-free perfume oil microemulsion as claimed in claim 1, wherein
    the at least one vicinal diol (b) is 1,2-hexanediol
    or
    the perfume oil microemulsion comprises two or more vicinal diols (b), wherein two of the vicinal diols (b) are 1,2-pentanediol and 1,2-octanediol.

6. The ethanol-free perfume oil microemulsion as claimed in claim 5, wherein the perfume oil microemulsion comprises two or more vicinal diols (b), wherein two of the vicinal diols (b) are 1,2-pentanediol and 1,2-octanediol, and wherein the ratio of the total amount of 1,2-pentanediol to 1,2-octanediol in the perfume oil microemulsion, based on weight, is in the range from 6:1 to 2:1.

7. The ethanol-free perfume oil microemulsion as claimed in claim 1, wherein the perfume oil microemulsion comprises the solvents (c) which are isobutyric acid-1-hydroxy-2,2,4-trimethyl-3-pentyl ester and isobutyric acid-3-hydroxy-2,2,4-trimethyl-1-pentyl ester.

8. The ethanol-free perfume oil microemulsion as claimed in claim 7, wherein the ratio of the total amount of isobutyric acid-1-hydroxy-2,2,4-trimethyl-3-pentyl ester to isobutyric acid-3-hydroxy-2,2,4-trimethyl-1-pentyl ester, based on weight, is in the range from 99:1 to 1:99.

9. The ethanol-free perfume oil microemulsion as claimed in claim 1, wherein, in each case relative to the total weight of the perfume oil microemulsion,
    the total amount of water (a) in the perfume oil microemulsion is 30 to 90 wt. %, and/or
    the total amount of vicinal diols (b) in the perfume oil microemulsion is 5 to 50 wt. %, and/or
    the total amount of solvents (c) in the perfume oil microemulsion is 1 to 20 wt. %, and/or
    the total amount of odor essences (d) in the perfume oil microemulsion is 1 to 50 wt. %.

10. An article comprising an ethanol-free perfume oil microemulsion as claimed in claim 1.

11. The article as claimed in claim 10, wherein the article is selected from the group consisting of eau de toilette and air fresheners.

12. The article as claimed in claim 11, wherein the article is selected from the group consisting of eau de toilette, room and laundry sprays.

13. The ethanol-free perfume oil microemulsion as claimed in claim 1, wherein, in each case relative to the total weight of the perfume oil microemulsion,
    the total amount of water (a) in the perfume oil microemulsion is 40 to 70 wt. %,
    and/or
    the total amount of vicinal diols (b) in the perfume oil microemulsion is 10 to 40 wt. %,
    and/or
    the total amount of solvents (c) in the perfume oil microemulsion is 2 to 10 wt. %,
    and/or
    the total amount of odor essences (d) in the perfume oil microemulsion is 4 to 10 wt. %.

14. A method of reducing the stickiness of an ethanol-free perfume oil microemulsion, comprising:
    providing an ethanol-free perfume oil microemulsion comprising
        (a) water;
        (b) at least one vicinal diol; and
        (d) at least one odor essence; and
    adding an amount of (c) isobutyric acid-1-hydroxy-2,2,4-trimethyl-3-pentyl ester, isobutyric acid-3-hydroxy-2,2,4-trimethyl-1-pentyl ester, or a mixture thereof to the perfume oil microemulsion that is sufficient to reduce the stickiness of the perfume oil microemulsion.

15. The method as claimed in claim 14, further comprising adding a mixture comprising isobutyric acid-1-hydroxy-2,2,4-trimethyl-3-pentyl ester and isobutyric acid-3-hydroxy-2,2,4-trimethyl-1-pentyl ester to the perfume oil microemulsion.

16. The method as claimed in claim 15, wherein the ratio of the total amount of isobutyric acid-1-hydroxy-2,2,4-trimethyl-3-pentyl ester to isobutyric acid-3-hydroxy-2,2,4-trimethyl-1-pentyl ester in the mixture, based on weight, is in the range from 99:1 to 1:99.

17. The method as claimed in claim 14, wherein the perfume oil microemulsion comprises:
    one vicinal diol, wherein the vicinal diol is 1,2-hexanediol;
    or
    two or more vicinal diols, wherein two of the vicinal diols are 1,2-pentanediol and 1,2-octanediol, and wherein the ratio of the total amount of 1,2-pentanediol to 1,2-octanediol in the perfume oil microemulsion, based on weight, is in the range from 6:1 to 2:1.

18. The method as claimed in claim 14, wherein the perfume oil microemulsion comprises one or more vicinal diols selected from the group consisting of 1,2-pentanediol, 1,2-hexanediol, 1,2-heptanediol and 1,2-octanediol.

* * * * *